(12) United States Patent
Hallen et al.

(10) Patent No.: US 10,492,873 B2
(45) Date of Patent: Dec. 3, 2019

(54) MEDICAL SPATIAL ORIENTATION SYSTEM

(71) Applicant: Novartis AG, Basel (CH)

(72) Inventors: Paul Hallen, Colleyville, TX (US); Joshua Anderson, Keller, TX (US)

(73) Assignee: Novartis AG, Basel (CH)

( * ) Notice: Subject to any disclaimer, the term of this patent is extended or adjusted under 35 U.S.C. 154(b) by 247 days.

(21) Appl. No.: 15/724,948

(22) Filed: Oct. 4, 2017

(65) Prior Publication Data

US 2018/0110571 A1 Apr. 26, 2018

Related U.S. Application Data

(60) Provisional application No. 62/412,648, filed on Oct. 25, 2016.

(51) Int. Cl.
*A61B 34/30* (2016.01)
*A61B 90/00* (2016.01)
(Continued)

(52) U.S. Cl.
CPC .............. *A61B 34/30* (2016.02); *A61B 17/00* (2013.01); *A61B 34/20* (2016.02); *A61B 34/37* (2016.02);
(Continued)

(58) Field of Classification Search
CPC ......... A61B 34/30; A61B 34/74; A61B 34/37; A61B 90/361; A61B 17/00; A61B 34/20; A61B 2034/2048; A61B 90/98; A61B 2017/00207; A61B 2090/371; A61B 2034/301; A61B 2090/373; A61B 2034/2055; A61B 2034/2065;
(Continued)

(56) References Cited

U.S. PATENT DOCUMENTS 5,491,510 A * 2/1996 Gove ................. H04N 5/23293
348/77
5,558,619 A * 9/1996 Kami ................. A61B 1/00006
600/106
(Continued)

FOREIGN PATENT DOCUMENTS

CN 105100712 A 11/2015
WO 2015171614 A1 11/2015

*Primary Examiner* — Jaime Figueroa

(57) ABSTRACT

A system and method for medical spatial orientation is disclosed including a robotic arm; an image sensor coupled to the robotic arm; a visualization headset; and a computing subsystem coupled to the robotic arm and the visualization headset. The computing subsystem includes a processor; a non-transitory machine-readable medium communicatively coupled to the processor; and instructions stored on the non-transitory machine-readable medium that, when loaded and executed by the processor, cause the processor to create a first image of a first portion of a surgical field at an image sensor coupled to the robotic arm; detect a movement of a visualization headset indicating a second portion of the surgical field; determine a movement of the robotic arm to position the image sensor at the second portion of the surgical field; move, based on the determination, the robotic arm; and create a second image of the second portion of the surgical field.

20 Claims, 4 Drawing Sheets

(51) Int. Cl.
*G02B 27/01* (2006.01)
*A61B 34/20* (2016.01)
*A61B 90/50* (2016.01)
*A61B 17/00* (2006.01)
*A61B 34/37* (2016.01)
*A61B 34/00* (2016.01)
*A61B 90/98* (2016.01)

(52) U.S. Cl.
CPC ............ *A61B 34/74* (2016.02); *A61B 90/361* (2016.02); *G02B 27/017* (2013.01); *G02B 27/0176* (2013.01); *A61B 90/98* (2016.02); *A61B 2017/00207* (2013.01); *A61B 2017/00216* (2013.01); *A61B 2034/2048* (2016.02); *A61B 2034/2055* (2016.02); *A61B 2034/2065* (2016.02); *A61B 2034/301* (2016.02); *A61B 2090/367* (2016.02); *A61B 2090/371* (2016.02); *A61B 2090/373* (2016.02); *A61B 2090/502* (2016.02); *A61B 2560/0487* (2013.01); *A61B 2562/0219* (2013.01); *G02B 2027/014* (2013.01); *G02B 2027/0138* (2013.01)

(58) Field of Classification Search
CPC ...... A61B 2090/367; A61B 2562/0219; A61B 2090/502; A61B 2017/00216; A61B 2560/0487; G02B 27/0176; G02B 27/017; G02B 2027/0138; G02B 2027/014

USPC .................................................. 700/245, 253

See application file for complete search history.

(56) References Cited

U.S. PATENT DOCUMENTS

| | | | | |
|---|---|---|---|---|
| 5,836,869 | A * | 11/1998 | Kudo | A61B 1/00039 600/173 |
| 5,876,325 | A * | 3/1999 | Mizuno | A61B 1/00048 600/102 |
| 5,917,460 | A * | 6/1999 | Kodama | G02B 27/0093 345/7 |
| 6,101,038 | A * | 8/2000 | Hebert | G02B 27/017 345/30 |
| 6,958,746 | B1 * | 10/2005 | Anderson | H04N 13/296 345/161 |
| 8,378,924 | B2 * | 2/2013 | Jacobsen | G02B 27/0172 345/7 |
| 8,681,095 | B2 * | 3/2014 | Ogawa | A61B 1/00131 345/156 |
| 10,028,651 | B2 * | 7/2018 | Tesar | A61B 90/361 |
| 10,285,765 | B2 * | 5/2019 | Sachs | A61B 17/00234 |
| 10,365,711 | B2 * | 7/2019 | Fuchs | G06F 3/012 |
| 2001/0006376 | A1 * | 7/2001 | Numa | G02B 27/017 345/7 |
| 2002/0082498 | A1 * | 6/2002 | Wendt | G06F 19/3418 600/411 |
| 2003/0179308 | A1 * | 9/2003 | Zamorano | A61B 5/00 348/333.12 |
| 2005/0156817 | A1 * | 7/2005 | Iba | G02B 27/0093 345/8 |
| 2006/0119539 | A1 * | 6/2006 | Kato | G02B 27/0176 345/8 |
| 2009/0036902 | A1 * | 2/2009 | DiMaio | A61B 34/10 606/130 |
| 2011/0234484 | A1 * | 9/2011 | Ogawa | A61B 1/00039 345/156 |
| 2011/0238079 | A1 * | 9/2011 | Hannaford | G06F 3/011 606/130 |
| 2015/0306340 | A1 * | 10/2015 | Giap | G16H 40/63 600/301 |
| 2015/0317830 | A1 | 11/2015 | Kihara et al. | |
| 2016/0225192 | A1 * | 8/2016 | Jones | G06F 3/012 |
| 2017/0202628 | A1 * | 7/2017 | Dell | A61B 34/32 |

* cited by examiner

US 10,492,873 B2

MEDICAL SPATIAL ORIENTATION SYSTEM

TECHNICAL FIELD

The present invention generally relates to surgical methods and, in particular, to systems and methods for a medical spatial orientation system.

BACKGROUND

Medical procedures are often performed using a microscope to magnify the surgical field. The position of the microscope is fixed in the vertical direction and may be moved horizontally to view different portions of the surgical field. The medical personnel may perform the medical procedure while viewing the surgical field in the microscope.

SUMMARY OF THE INVENTION

In accordance with some embodiments of the present disclosure, a medical spatial orientation system is disclosed. The medical spatial orientation system includes a robotic arm; an image sensor coupled to the robotic arm; a visualization headset; and a computing subsystem coupled to the robotic arm and the visualization headset. The computing subsystem includes a processor; a non-transitory machine-readable medium communicatively coupled to the processor; and instructions stored on the non-transitory machine-readable medium. The instructions, when loaded and executed by the processor, cause the processor to create a first image of a first portion of a surgical field at an image sensor coupled to the robotic arm; detect a movement of a visualization headset indicating a second portion of the surgical field; determine a movement of the robotic arm to position the image sensor at the second portion of the surgical field; move, based on the determination, the robotic arm; and create a second image of the second portion of the surgical field.

In accordance with another embodiment of the present disclosure, a medical spatial orientation system is disclosed. The medical spatial orientation system includes a processor; a non-transitory machine-readable medium communicatively coupled to the processor; and instructions stored on the non-transitory machine-readable medium. The instructions, when loaded and executed by the processor, cause the processor to create a first image of a first portion of a surgical field at an image sensor coupled to a robotic arm; detect a movement of a visualization headset indicating a second portion of the surgical field; determine a movement of the robotic arm to position the image sensor at the second portion of the surgical field; move, based on the determination, the robotic arm; and create a second image of the second portion of the surgical field.

In accordance with a further embodiment of the present disclosure, a method for operating a medical spatial orientation system is disclosed. The method includes creating a first image of a first portion of a surgical field at an image sensor coupled to a robotic arm; detecting a movement of a visualization headset indicating a second portion of the surgical field; determining a movement of the robotic arm to position the image sensor at the second portion of the surgical field; moving, based on the determination, the robotic arm; and creating a second image of the second portion of the surgical field.

The above systems may be used with the above methods and vice versa. In addition, any system described herein may be used with any method described herein and vice versa.

BRIEF DESCRIPTION OF THE DRAWING

For a more complete understanding of the present disclosure and its features and advantages, reference is now made to the following description, taken in conjunction with the accompanying drawings, in which.

DETAILED DESCRIPTION

The present disclosure provides a medical spatial orientation system that allows medical personnel to view a surgical field during a medical procedure. The surgical field may be viewed via images created using an image sensor. The images created by the image sensor may be displayed on an external display or using a visualization headset worn by the medical personnel. Use of the medical spatial orientation system may allow medical personnel to perform medical procedures in a more ergonomic position, may provide off-angle viewing of the surgical field, may provide a more natural viewing control that is based on the movement of the head of the medical personnel. Additionally, the medical spatial orientation system may allow the medical personnel to input commands and menu selections for a surgical application in a hands-free manner.

A further description of the embodiments of the medical spatial orientation system, components thereof, and methods of its uses is presented with reference to FIGS. 1 through 5.

Figure 1:
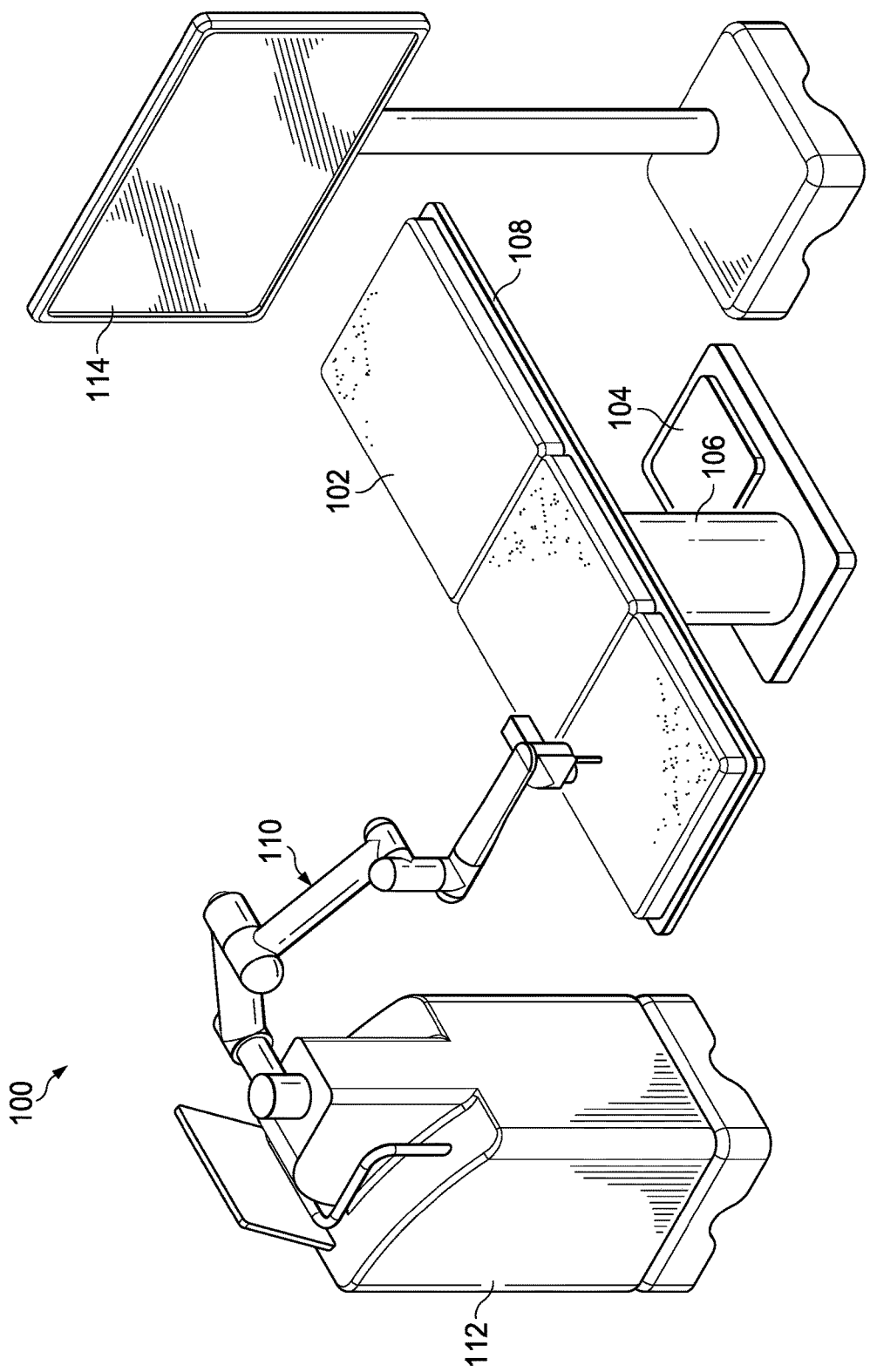
FIG. 1 is a perspective view of an operating room including a medical spatial orientation system.

FIG. 1 is a perspective view of an operating room including a medical spatial orientation system. Operating room 100 may include operating table 102. Operating table 102 may include base 104, column 106, and table top 108. Base 104 may be attached to the floor of operating room 100 or may be portable such that operating table 102 may be removed from operating room 100 or repositioned in operating room 100. Column 106 may be coupled to base 104. Column 106 may include hydraulics or motors that allow the height of column 106 to be adjusted such that table top 108 moves vertically relative to base 104. Table top 108 provides a surface on which a patient is positioned during a medical procedure. Table top 108 may be rotatable on column 106 to allow the medical personnel to position the patient for the medical procedure. While table top 108 is shown in FIG. 1 as being relatively flat, table top 108 may be adjustable to elevate portions of the patient's body relative to the remainder of the patient's body.

Figure 2:
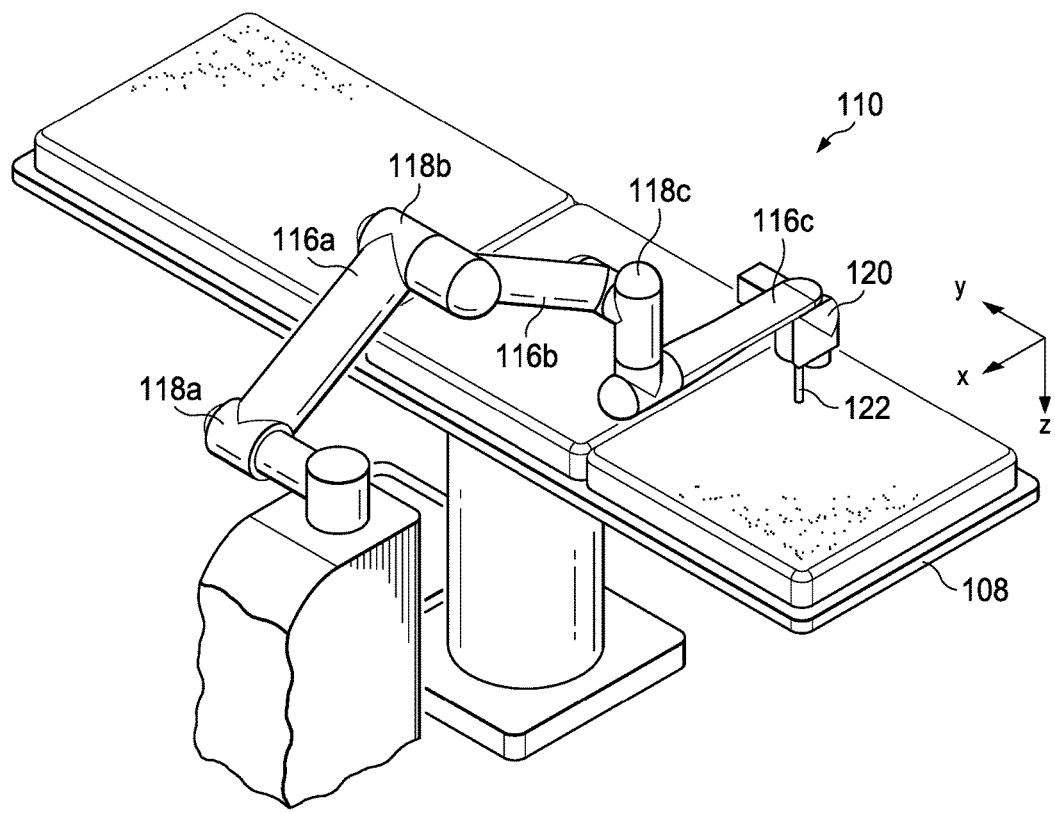
FIG. 2 is a perspective view of the robotic arm shown in FIG. 1.

Operating room 100 may include robotic arm 110. Robotic arm 110 may include a combination of joints and links (as shown in FIG. 2) which allow robotic arm 110 to move around the patient during the medical procedure. Robotic arm 110 may have one or more image sensors (shown in FIG. 2) coupled to robotic arm 110. As robotic arm 110 moves around the patient, the image sensor may create one or more images of the portions of the patient of interest for the medical procedure. Robotic arm 110 and the image sensor coupled to robotic arm 110 are described in further detail in FIG. 2.

Robotic arm 110 may be coupled to console 110. Console 112 may include equipment for moving the joints and links in robotic arm 110 during the medical procedure. Console 112 may also include computing equipment for receiving images from the image sensor coupled to robotic arm 110. The computing equipment in console 112 may process the images and display the images to the medical personnel in operating room 100. For example, the images may be displayed on external display 114. External display 114 may be any suitable display device used to display the images created by image sensor 122 to medical personnel. For example, external display 114 may be a liquid crystal display, a light emitting diode display, or a cathode ray tube display. The images may also be displayed at a headset (shown in FIG. 3) worn by the medical personnel.

The movement of robotic arm 110 may be controlled by medical personnel using a visualization headset. The visualization headset (shown in FIG. 3) may be worn by the medical personnel and may include accelerometers to track the movements of the head of the medical personnel in three dimensions. For example, when the medical personnel views an image from the image sensor on robotic arm 110 and moves her head to the right, robotic arm 110 moves such that the image sensor move to the right and the medical personnel can then view an image of a portion of the patient's body that is to the right of the portion shown in the original image.

FIG. 2 is a perspective view of the robotic arm shown in FIG. 1. Robotic arm 110 includes links 116a-116c, joints 118a-118c, and head 120. Links 116 span between joints 118. One or more joints 118 may move such that the position of head 120 changes relative to the patient. Joints 118 may include one or more motors (not expressly shown) that move joints 118. The motor may be activated to move joints 118 and thus move links 116. The motor may be any suitable type of motor including a stepper motor, an electric motor, a servomotor, a rotary actuator, a liner actuator, or any combination thereof. While three links 116 and three joints 118 are shown in FIG. 2, robotic arm 110 may include any number of links 116 and joints 118 to provide a range of movement of head 120 relative to the patient. For example, robotic arm 110 may be capable of moving head 120 in the x-direction, y-direction, and z-direction. Additionally, robotic arm 110 may be capable rotating head 120 relative to arm link 116c such that head 120 may be placed at any position relative to the patient.

Image sensor 122 may be coupled to head 120. Image sensor 122 may be any electronic device able to convert light to a digital image. For instance, it may be a digital camera, a light-to-digital sensor, a semiconductor charge-coupled device (CCD), a complementary metal-oxide-semiconductor (CMOS) device, an N-type metal-oxide-semiconductor (NMOS) device, or another electronic device containing an array of photodiodes as part of one or more integrated circuits. Image sensor 122 may contain additional lenses or other elements to assist with image creation. Image sensor 122 may produce a digital image with sufficient resolution to produce a usable image. For example, image sensor 122 may have a minimum horizontal resolution of approximately 2,000 pixels. Image sensor 122 may be a three dimensional camera system including at least two image sensors such that a three dimensional image can be displayed to the medical personnel. Image sensor 122 may be capable of high dynamic range (HDR) imaging. HDR imaging produces an image with a greater dynamic range of luminosity than a standard image. Such imaging may be used when image sensor 122 is creating an image that includes bright and dark portions. For example, during medical procedures on a human eye, some portions of the eye are bright while other portions are dark. HDR imaging may allow all portions of the eye to be visible in the image.

Image sensor 122 may include a zoom lens system such that the portion of the surgical field included in the image created by image sensor 122 can be magnified. When equipped with a zoom lens system, image sensor 122 may be used in place of a traditional microscope during a medical procedure.

Figure 3:
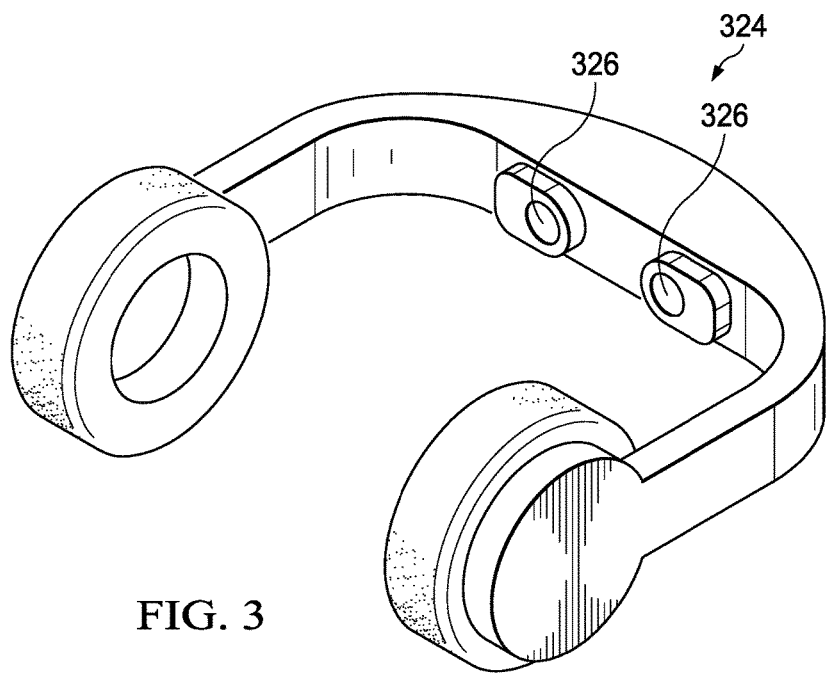
FIG. 3 is a perspective view of a visualization headset designed for use with the medical spatial orientation system shown in FIG. 1.
Figure 4:
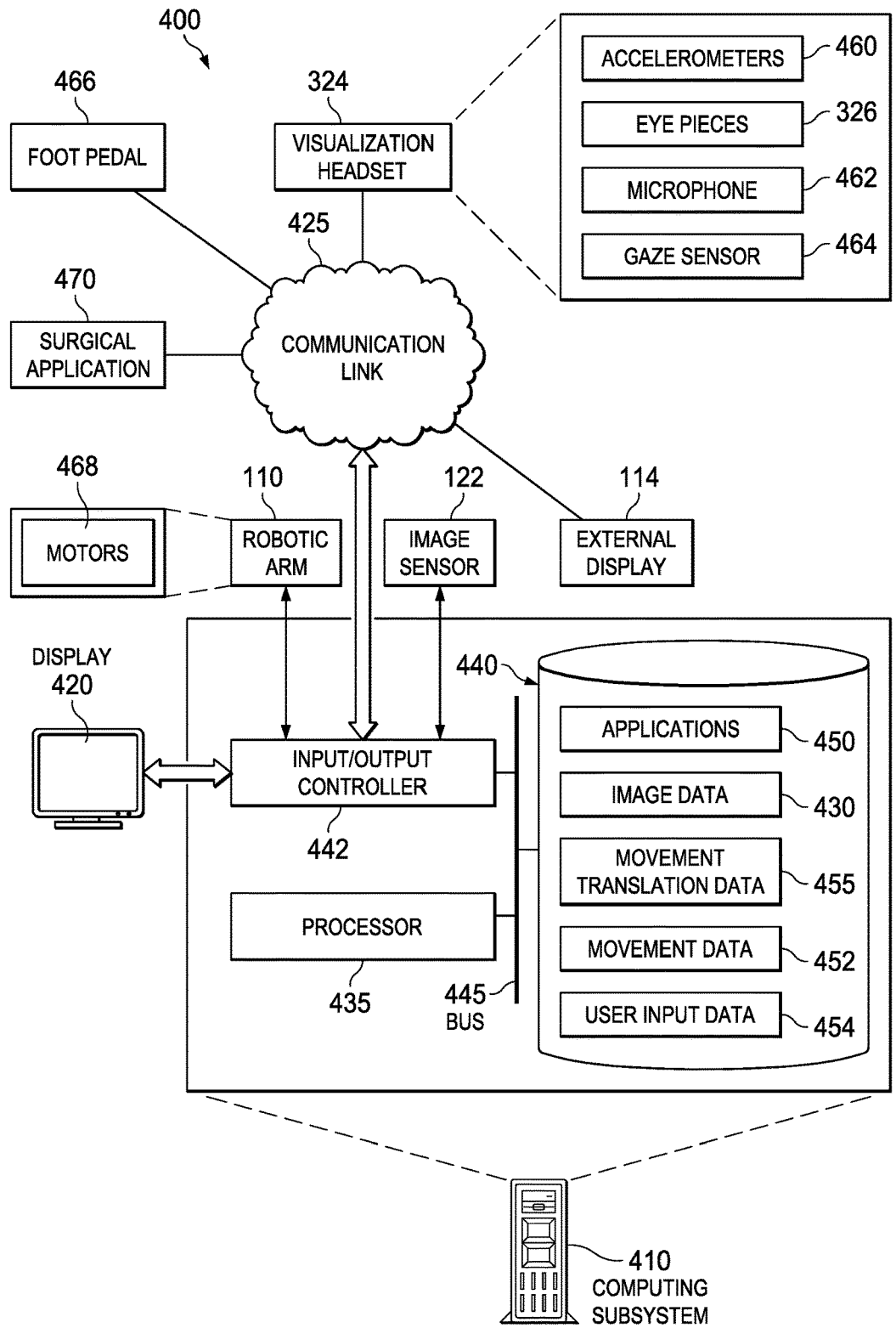
FIG. 4 is a block diagram of the medical spatial orientation system shown in FIGS. 1-3.

Image sensor 122 may transmit the image to a computing subsystem (as shown in FIG. 4). The computing subsystem may process the image and transmit the image to an external display, such as external display 114 shown in FIG. 1, to a headset worn by medical personnel (as shown in FIG. 3), or both. Image sensor 122 may be communicate with the computing subsystem using any suitable wired or wireless technology including a wireless or a wired network, a Local Area Network (LAN), a Wide Area Network (WAN), a private network, a public network (such as the Internet), a wireless network, a network that includes a satellite link, a serial link, a wireless link (e.g., infrared, radio frequency, BLUETOOTH, or others), a parallel link, or any combination thereof. The computing subsystem may communicate with the external display and/or the headset using any suitable wired or wireless technology including a wireless or a wired network, a LAN, a WAN, a private network, a public network (such as the Internet), a wireless network, a network that includes a satellite link, a serial link, a wireless link (e.g., infrared, radio frequency, BLUETOOTH, or others), a parallel link, or any combination thereof.

FIG. 3 is a perspective view of a visualization headset designed for use with the medical spatial orientation system shown in FIG. 1. Headset 324 may include eyepieces 326. Eyepieces 326 may include displays for presenting images created by an image sensor, such as image sensor 122 shown in FIG. 2, to the medical personnel wearing headset 324. Eyepieces 326 may include lights, such as LEDs, that project an image created by the image sensor onto the retina of the medical personnel wearing headset 324. Headset 324 may allow the medical personnel to view the surgical field during the medical procedure.

Headset 324 may also include accelerometers (not expressly shown) that detect the movement of the head of the medical personnel wearing headset 324. The accelerometers may track the movement of headset 324 in three dimensional space. Headset 324 may communicate information about the movements of headset 324 to a computing subsystem (shown in FIG. 4). The computing subsystem may process the information about the movement of headset 324 to determine the corresponding movements of a robotic arm, such as robotic arm 110 shown in FIGS. 1 and 2, such that robotic arm moves based on the movement of headset 324.

During a medical procedure, the medical personnel, such as a surgeon, may wear headset 324. The image presented to the medical personnel may be a magnified image such that the medical personnel can view the surgical field without the use of a microscope. When the medical personnel wants to view a different portion of the surgical field, the medical personnel may move her head towards the desired portion of the surgical field. The accelerometers in headset 324 may detect the movements of headset 324 and communicate the movements to a computing subsystem. The computing subsystem may process the movements and may determine the movements of the robotic arm that will position the image sensor coupled to the robotic arm near the desired portion of the surgical field. The computing subsystem may then command the robotic arm to move. The image sensor may create a new image of the desired portion of the surgical field. The new image may be communicated through the computing subsystem to headset 324 and the image may be displayed to the medical personnel. The process for using the medical spatial orientation system is described in more detail in FIG. 5.

Headset 324 may also display menus, command options, or both. For example, headset 324 may display a menu related to the zoom level at which the image is presented to the medical personnel. The menu options (e.g., "Zoom-In" or "Zoom-Out") may be selected by any suitable method including via voice command, gaze time, foot pedal, sensor-based sterile disposable gloves, sensor-based finger sleeves, or any combination thereof. The sensors may include RFID sensors for identification, pressure sensors for selection, accelerometer based sensors for gesture control, or any combination thereof. For example, headset 324 may include a microphone (not expressly shown) to detect voice commands from the medical personnel. Additionally, headset 324 may include sensors (not expressly shown) to track the eye position to determine where the medical personnel is looking and, if the medical personnel looks at a menu option for a period of time, the menu option is selected. The period of time may be two seconds, three seconds, five seconds, or any suitable period of time. Further, a foot pedal may be coupled to the computing subsystem. The medical personnel may depress the foot pedal to select a menu option. The selection methods may be combined. For example, selection may be based on a 1-second gaze to select a menu option combined with a foot pedal depression to confirm the selection.

FIG. 4 is a block diagram of the medical spatial orientation system shown in FIGS. 1-3. Medical spatial orientation system 400 may include computing subsystem 410, robotic arm 110, external display 114, image sensor 122, visualization headset 324, display 420, communication link 425, foot pedal 466, and surgical application 470. Some or all of the components of computing subsystem 410 may be housed in a console, such as console 112 shown in FIG. 1. Image sensor 122 may create images of the surgical field. Image sensor 122 may then transmit the images to computing subsystem 410 for storage as image data 430 as discussed in further detail below. Image data 430 may additionally include information related to the zoom level of the image. Image sensor 122 may be any electronic device able to convert light to a digital image. For instance, it may be a digital camera, a light-to-digital sensor, a semiconductor charge-coupled device (CCD), a complementary metal-oxide-semiconductor (CMOS) device, an N-type metal-oxide-semiconductor (NMOS) device, or another electronic device containing an array of photodiodes as part of one or more integrated circuits. Image sensor 122 may contain additional lenses or other elements to assist with image capture. Image sensor 122 produces a digital image with sufficient resolution to produce a usable corrected image, even after image processing.

All or part of computing subsystem 410 may operate as a component of or independent of the medical spatial orientation system or independent of any other components shown in FIG. 1. Computing subsystem 410 may include processor 435, memory 440 and input/output controllers 442 communicatively coupled by bus 445. Processor 435 may include hardware for executing instructions, such as those making up a computer program, such as application 450. As an example and not by way of limitation, to execute instructions, processor 435 may retrieve (or fetch) the instructions from an internal register, an internal cache, and/or memory 440; decode and execute them; and then write one or more results to an internal register, an internal cache, and/or memory 440. This disclosure contemplates processor 435 including any suitable number of any suitable internal registers, where appropriate. Where appropriate, processor 435 may include one or more arithmetic logic units (ALUs); be a multi-core processor; or include one or more processors 435. Although this disclosure describes and illustrates a particular processor, this disclosure contemplates any suitable processor.

Processor 435 may execute instructions, for example, to process movement information from visualization headset 324 to command movements of robotic arm 110 of a medical spatial orientation system. For example, processor 435 may run application 450 by executing or interpreting software, scripts, programs, functions, executables, or other modules contained in application 450. Processor 435 may perform one or more operations related to FIG. 5. Input data received by processor 435 or output data generated by processor 435 may include image data 430, movement data 452, user input data 454, and movement translation data 455.

Memory 440 may include, for example, random access memory (RAM), a storage device (e.g., a writable read-only memory (ROM) or others), a hard disk, a solid state storage device, or another type of storage medium. Computing subsystem 410 may be preprogrammed or it may be programmed (and reprogrammed) by loading a program from another source (e.g., from a CD-ROM, from another computer device through a data network, or in another manner). Input/output controller 442 may be coupled to input/output devices (e.g., display 420, robotic arm 110, image sensor 122, a mouse, a keyboard, or other input/output devices) and to communication link 425. The input/output devices may receive and transmit data in analog or digital form over communication link 425.

Memory 440 may store instructions (e.g., computer code) associated with an operating system, computer applications, and other resources. Memory 440 may also store application data and data objects that may be interpreted by one or more applications or virtual machines running on computing subsystem 410. For example, image data 430, movement data 452, user input data 454, movement translation data 455, and applications 450 may be stored in memory 440. In some implementations, a memory of a computing device may include additional or different data, applications, models, or other information.

Image data 430 may include information related to images created by image sensor 122 that may be used to display to medical personnel wearing virtualization headset 324 via eye pieces 326, viewing external display 114, or both. Movement data 452 may include information related to the movements of virtualization headset 324. For example, movement data 452 may include information obtained from accelerometers 460. User input data 454 may include information related to menu or command selections selected by the medical personnel wearing virtualization headset 324. For example, menu or command selections may be input using microphone 462, gaze sensor 464, foot pedal 466, or any combination thereof, as described with reference to FIG. 3. Movement translation data 455 may include information related to translating the movements of virtualization headset 324 into corresponding movements of robotic arm 110 such that robotic arm 110 moves image sensor 122 based on the movement of virtualization headset 324. Movement translation data 455 may be calibrated based on the type of medical procedure being performed. For example, for medical procedures involving small surgical fields, the movement of virtualization headset 324 may correspond to a small movement of image sensor 122 while in a medical procedure involving a larger surgical field, the movement of virtualization headset 324 may correspond to a larger movement of image sensor 122. Values from image data 430, movement data 452, user input data 454, and movement translation data 455 may be used to calculate the amount of movement of robotic arm 110 used to move image sensor 122 to a new position based on the movement of virtualization headset 324.

Applications 450 may include software applications, scripts, programs, functions, executables, or other modules that may be interpreted or executed by processor 435. Applications 450 may include machine-readable instructions for performing one or more operations related to FIG. 5. Applications 450 may include machine-readable instructions for calculating the movements of robotic arm 110 used to move image sensor 122 based on the movements of visualization headset 324. For example, applications 450 may be configured to analyze image data 430, movement data 452, user input data 454, and movement translation data 455 to determine the movements of robotic arm 110 that correspond to the movements of visualization headset 324. Applications 450 may generate output data and store output data in memory 440, in another local medium, or in one or more remote devices (e.g., by sending output data via communication link 425). For example, applications 450 may send a movement command to robotic arm 110. One or more motors 468 in robotic arm 110 may move based on the command.

Motor 468 may be coupled to one or more joints in robotic arm 110, such as joints 118 shown in FIG. 2. Motor 468 may be activated to change the position of the one or more joints and thus change the position of image sensor 122. Motor 468 may be any suitable type of motor including a stepper motor, an electric motor, a servomotor, a rotary actuator, a liner actuator, or any combination thereof. The position of image sensor 122 may be recorded in movement translation data 455, discussed in further detail below.

Communication link 425 may include any type of communication channel, connector, data communication network, or other link. For example, communication link 425 may include a wireless or a wired network, a Local Area Network (LAN), a Wide Area Network (WAN), a private network, a public network (such as the Internet), a wireless network, a network that includes a satellite link, a serial link, a wireless link (e.g., infrared, radio frequency, or others), a parallel link, or another type of data communication network.

External display 114 may be any suitable display device used to display the images created by image sensor 122 to medical personnel. For example, external display 114 may be a liquid crystal display, a light emitting diode display, or a cathode ray tube display. External display 114 may display three dimensional images, HDR images, or both. External display 114 may be coupled to computing subsystem 410 via communications link 425.

Processor 435 may analyze images created by image sensor 122 saved in image data 430 and movement data 452 detected by accelerometers 460 to determine the movement of visualization headset 324. Processor 435 may then use movement translation data 455 to determine the movement of robotic arm 110 that corresponds with positioning image sensor 122 in a location corresponding to the movement of visualization headset 324. Further, processor 435 may transmit a menu selection received from visualization headset 324 to surgical application 470 via communications link 425. Surgical application 470 may be any suitable surgical application including an optical coherence tomography application, a medical ultrasonography application, endoscopy application that provides an alternate view of a micro-area, or any combination thereof. Surgical application 470 may provide a picture-in-picture view of the surgical field, a split-screen view of the surgical field, or any combination thereof.

Figure 5:
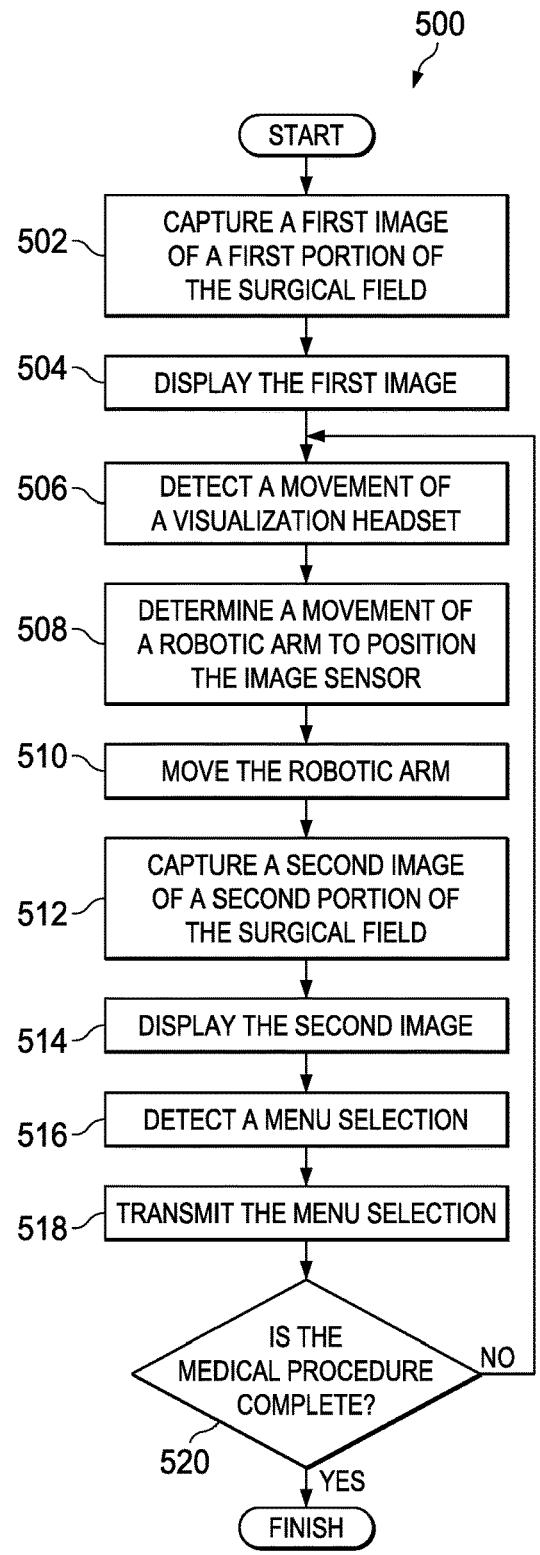
FIG. 5 is a flow chart of a method of operating a medical spatial orientation system.

FIG. 5 is a flow chart of a method of operating a medical spatial orientation system. The steps of method 500 may be performed by a person, various computer programs, models or any combination thereof, configured to control and analyze information from medical systems, apparatuses and devices. The programs and models may include instructions stored on a computer readable medium and operable to perform, when executed, one or more of the steps described below. The computer readable media may include any system, apparatus or device configured to store and retrieve programs or instructions such as a hard disk drive, a compact disc, flash memory or any other suitable device. The programs and models may be configured to direct a processor or other suitable unit to retrieve and execute the instructions from the computer readable media. For example, the programs and models may be one of the applications in applications 450 shown in FIG. 4. For illustrative purposes, method 500 is described with respect to a medical spatial orientation system similar to medical spatial orientation system 100 illustrated in FIG. 1; however, method 500 may be used to operate any suitable medical spatial orientation system.

Method 500 may begin at step 502 where the medical spatial orientation system may create a first image of a first portion of a surgical field. The first image may be created using an image sensor coupled to a robotic arm, such as image sensor 122 coupled to robotic arm 110 shown in FIG. 2. The first image may be created at any zoom level according to a setting entered by medical personnel. The first image may be a three dimensional image, a high dynamic range image, or both.

At step 504, the medical spatial orientation system may display the first image created at step 502. The first image may be displayed using an eyepiece of a visualization headset, such as eyepiece 326 shown in FIG. 3, on an external display, such as external display 114 shown in FIG. 1, or any combination thereof.

At step 506, the medical spatial orientation system may detect a movement of the visualization headset. The visualization headset may be worn by medical personnel during a medical procedure. Movement of the visualization headset may be detected by one or more accelerometers included in the visualization headset. The movements of the visualization headset may indicate a second portion of the surgical field of which to create an image.

At step 508, the medical spatial orientation system may determine a movement of a robotic arm that will position the image sensor at the second portion of the surgical field. The movement of the robotic arm may be based on the movement of the visualization headset. For example, if the accelerometers in the visualization headset detect a movement to the right, indicating that the medical personnel wearing the visualization headset requests an image of a portion of the surgical field to the right of the portion shown in the first image, the medical spatial orientation system may determine the movement of the robotic arm that will position the image sensor such that an image of the portion of the surgical field to the right of the first portion can be created.

At step 510, the medical spatial orientation system may move the robotic arm such that the image sensor is positioned at the second portion of the surgical field. The robotic arm may be moved by motors coupled to one or more joints of the robotic arm. The motors may move the joints to move the robotic arm.

At step 512, the medical spatial orientation system may create a second image of a second portion of the surgical field using the image sensor coupled to the robotic arm. The second image may be created at any zoom level according to a setting entered by medical personnel. The second image may be a three dimensional image, a high dynamic range image, or both.

At step 514, the medical spatial orientation system may display the second image created at step 512. The second image may be displayed using an eyepiece of a visualization headset, such as eyepiece 326 shown in FIG. 3, on an external display, such as external display 114 shown in FIG. 1, or any combination thereof.

At step 516, the medical spatial orientation system may detect a menu selection. The menu selection may be detected using a gaze sensor, a microphone, a foot pedal, or any combination thereof. For example, the visualization headset may display a menu related to the zoom level at which the image is presented to the medical personnel. The menu options (e.g., "Zoom-In" or "Zoom-Out") may be selected by detecting voice commands from the medical personnel. Additionally, the menu options may be selected by tracking the eye position of the medical personnel to determine where the medical personnel is looking and, if the medical personnel looks at a menu option for a period of time, the menu option is selected. Further, the menu option may be selected by depressing a foot pedal coupled to the medical spatial orientation system.

At step 518, the medical spatial orientation system may transmit the menu selection to a surgical application. For example, the surgical application may be an optical coherence tomography ("OCT") application and the medical spatial orientation system may transmit a command to cause the OCT application to capture an OCT image.

At step 520, the medical spatial orientation system may determine if the medical procedure is complete. If the medical procedure is complete, method 500 may end. If the medical procedure is not complete, method 500 may return to step 506 to continue detecting the movements of the visualization headset.

Modifications, additions, or omissions may be made to method 500 without departing from the scope of the present disclosure. For example, the order of the steps may be performed in a different manner than that described and some steps may be performed at the same time. For example, steps 514 and 516 may be performed simultaneously with steps 506-512. Additionally, each individual step may include additional steps without departing from the scope of the present disclosure.

Although the present disclosure has been described with several embodiments, various changes and modifications may be suggested to one skilled in the art. For example, table top 108 shown in FIG. 1 may be replaced with a chair or other suitable surface for placing a patient during a medical procedure. The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

The invention claimed is:

1. A medical spatial orientation system, comprising:
   a robotic arm;
   an image sensor coupled to the robotic arm;
   a visualization headset; and
   a computing subsystem coupled to the robotic arm and the visualization headset, the computing subsystem including:
      a processor;
      a non-transitory machine-readable medium communicatively coupled to the processor; and
      instructions stored on the non-transitory machine-readable medium, the instructions, when loaded and executed by the processor, cause the processor to:
         create a first image of a first portion of a surgical field at an image sensor coupled to the robotic arm;
         detect a movement of a visualization headset indicating a second portion of the surgical field;
         determine a movement of the robotic arm to position the image sensor at the second portion of the surgical field;
         move, based on the determination, the robotic arm; and
         create a second image of the second portion of the surgical field.

2. The medical spatial orientation system of claim 1, wherein the instructions further cause the processor to:
   detect a menu selection at the visualization headset; and
   transmit the menu selection to a surgical application.

3. The medical spatial orientation system of claim 1, wherein the instructions further cause the processor to display at least one of the first or the second image at the visualization headset.

4. The medical spatial orientation system of claim 1, wherein the instructions further cause the processor to display at least one of the first or the second image at an external display.

5. The medical spatial orientation system of claim 1, wherein detecting a movement of the visualization headset indicating the second portion of the surgical field includes detecting an acceleration of the visualization headset.

6. The medical spatial orientation system of claim 1, wherein at least one of the first or the second image is a high dynamic range image.

7. The medical spatial orientation system of claim 1, wherein at least one of the first or the second image is a three dimensional image.

8. A medical spatial orientation system, comprising:
   a processor;
   a non-transitory machine-readable medium communicatively coupled to the processor; and
   instructions stored on the non-transitory machine-readable medium, the instructions, when loaded and executed by the processor, cause the processor to:
      create a first image of a first portion of a surgical field at an image sensor coupled to a robotic arm;
      detect a movement of a visualization headset indicating a second portion of the surgical field;

determine a movement of the robotic arm to position the image sensor at the second portion of the surgical field;

move, based on the determination, the robotic arm; and create a second image of the second portion of the surgical field.

9. The medical spatial orientation system of claim 8, wherein the instructions further cause the processor to:

detect a menu selection at the visualization headset; and transmit the menu selection to a surgical application.

10. The medical spatial orientation system of claim 8, wherein the instructions further cause the processor to display at least one of the first or the second image at the visualization headset.

11. The medical spatial orientation system of claim 8, wherein the instructions further cause the processor to display at least one of the first or the second image at an external display.

12. The medical spatial orientation system of claim 8, wherein detecting a movement of the visualization headset indicating the second portion of the surgical field includes detecting an acceleration of the visualization headset.

13. The medical spatial orientation system of claim 8, wherein at least one of the first or the second image is a high dynamic range image.

14. The medical spatial orientation system of claim 8, wherein at least one of the first or the second image is a three dimensional image.

15. A method for operating a medical spatial orientation system, comprising:

creating a first image of a first portion of a surgical field at an image sensor coupled to a robotic arm;

detecting a movement of a visualization headset indicating a second portion of the surgical field;

determining a movement of the robotic arm to position the image sensor at the second portion of the surgical field;

moving, based on the determination, the robotic arm; and creating a second image of the second portion of the surgical field.

16. The method of claim 15, further comprising:

detecting a menu selection at the visualization headset; and transmitting the menu selection to a surgical application.

17. The method of claim 15, further comprising displaying at least one of the first or the second image at the visualization headset.

18. The method of claim 15, further comprising displaying at least one of the first or the second image at an external display.

19. The method of claim 15, wherein detecting a movement of the visualization headset indicating the second portion of the surgical field includes detecting an acceleration of the visualization headset.

20. The method of claim 15, wherein at least one of the first or the second image is a high dynamic range image.

* * * * *